United States Patent [19]

Bartley

[11] Patent Number: 4,661,643
[45] Date of Patent: Apr. 28, 1987

[54] HYDROGENOLYSIS PROCESS FOR THE PRODUCTION OF MONOETHYLENE GLYCOL MONOMETHYL ETHER, MONOETHYLENE GLYCOL AND ETHANOL

[75] Inventor: William J. Bartley, Charleston, W. Va.

[73] Assignee: Union Carbide Corporation, Danbury, Conn.

[21] Appl. No.: 736,535

[22] Filed: May 21, 1985

Related U.S. Application Data

[63] Continuation of Ser. No. 307,225, Sep. 30, 1981, abandoned.

[51] Int. Cl.$^4$ ............... C07C 41/01; C07C 31/08; C07C 31/20
[52] U.S. Cl. ............... 568/678; 568/866; 568/903; 568/907
[58] Field of Search ............... 568/678, 866, 903, 907

[56] References Cited

U.S. PATENT DOCUMENTS

| | | | |
|---|---|---|---|
| 1,953,548 | 4/1934 | Young et al. | 260/156 |
| 2,497,812 | 2/1950 | Copelin | 260/635 |
| 2,658,081 | 11/1953 | Emerson et al. | 260/615 |
| 2,768,978 | 10/1956 | Robertson | 260/635 |
| 3,833,634 | 9/1974 | Pruett et al. | 260/449 R |
| 3,975,449 | 8/1976 | Suzuki | 260/635 E |
| 4,088,700 | 5/1978 | Watts | 260/632 B |
| 4,091,041 | 5/1978 | Smith | 568/865 |

FOREIGN PATENT DOCUMENTS

| | | |
|---|---|---|
| 2434057 | 1/1976 | Fed. Rep. of Germany . |
| 2716690 | 10/1978 | Fed. Rep. of Germany . |
| 2900279 | 7/1980 | Fed. Rep. of Germany . |
| 2447363 | 1/1979 | France . |
| 2524674 | 6/1974 | Japan . |
| 109908 | 8/1979 | Japan . |

OTHER PUBLICATIONS

Davidova and Kraus *Journal of Catalysis*, 61, 1–6 (1980).

Primary Examiner—Howard T. Mars
Attorney, Agent, or Firm—Steven T. Trinker

[57] ABSTRACT

This invention relates to a process for selectively cleaving a polyalkylene glycol, e.g., diethylene glycol, containing at least one ether group therein at a carbon-to-oxygen covalent bond and independently at a carbon-to-carbon covalent bond by heating the polyalkylene glycol with molecular hydrogen in the presence of a hydrogenation catalyst containing ruthenium to produce at least one of monoethylene glycol monomethyl ether, monoethylene glycol and ethanol. The production rate of each of said monoethylene glycol monomethyl ether, monoethylene glycol and ethanol is at least about 10 moles/kilogram ruthenium/hour.

8 Claims, No Drawings

HYDROGENOLYSIS PROCESS FOR THE PRODUCTION OF MONOETHYLENE GLYCOL MONOMETHYL ETHER, MONOETHYLENE GLYCOL AND ETHANOL

This application is a continuation of prior U.S. application Ser. No. 307,225, filed Sept. 30, 1981, now abandoned.

BRIEF SUMMARY OF THE INVENTION

1. Technical Field

This invention is directed to the production of monoethylene glycol monomethyl ether, monoethylene glycol and ethanol at significantly high production rates by the hydrogenolysis of a polyalkylene glycol, e.g., diethylene glycol. The polyalkylene glycol is selectively cleaved at a carbon-to-oxygen covalent bond and independently at a carbon-to-carbon covalent bond by heating with molecular hydrogen in the presence of a hydrogenation catalyst containing ruthenium to produce at least one of monoethylene glycol monomethyl ether, monoethylene glycol and ethanol. The production rate of each of said monoethylene glycol monomethyl ether, monoethylene glycol and ethanol is at least about 10 moles/kilogram ruthenium/hour.

2. Background Art

It is known that monoethylene glycol is commercially produced by the hydrolysis of ethylene oxide which in turn is generated by the oxidation of ethylene, typically by the reaction of ethylene and oxygen over a silver containing catalyst. Other processes (noncommercial) for making monoethylene glycol involve reactions of carbon monoxide with hydrogen or formaldehyde, typically in the presence of a certain precious metal catalyst. Major by-products of the commercial oxide/glycol process are diethylene glycol and higher polyalkylene glycols in amounts up to 10 percent by weight of the total product mixture. However, diethylene glycol may or may not be a commercially desirable by-product. For instance, considerably more diethylene glycol by-product may be produced from the commercial oxide/glycol process than can be utilized profitably. In those instances where the production of diethylene glycol is commercially undesirable, any process capable of efficiently converting this by-product to monothylene glycol monomethyl ether, monoethylene glycol, ethanol or other valuable products at preferably high production rates would be highly desirable.

It has been found as a result of the present invention that polyalkylene glycols, e.g., diethylene glycol, can be selectively cleaved at a carbon-to-oxygen covalent bond and independently at a carbon-to-carbon covalent bond by heating the polyalkylene glycol with molecular hydrogen in the presence of a hydrogenation catalyst containing ruthenium to product at least one of monoethylene glycol monomethyl ether, monoethylene glycol and ethanol. The production rate of each of said monoethylene glycol monomethyl ether, monoethylene glycol and ethanol is at least about 10 moles/kilogram ruthenium/hour.

The following prior art references describe processes involving hydrogenolysis or cleaving with molecular hydrogen in the presence of a hydrogenation catalyst:

Japanese Patent Publication No. 25,246/74 describes selectively cleaving polyalkylene glycols, e.g., diethylene glycol, and polyalkylene glycol monoalkyl ethers at a carbon-to-carbon covalent bond by heating with molecular hydrogen in the presence of a nickel or palladium catalyst to give alkylene glycol monoalkyl ethers, e.g., monoethylene glycol monomethyl ether, polyalkylene glycol monoalkyl ethers, alkylene glycol dialkyl ethers and polyalkylene glycol dialkyl ethers. Lower polyalkylene glycols, monoethylene glycol, dimethyl ether and methane are described as being coproduced by this cleaving process. However, this patent does not disclose or teach the coproduction of ethanol resulting from the hydrogenolysis of a polyalkylene glycol.

German Pat. No. 2,900,279 describes selectively cleaving polyalkylene glycols, e.g., diethylene glycol, or monoethylene glycol monoalkyl or monoaryl ethers including their homologs at a carbon-to-carbon covalent bond with molecular hydrogen in the presence of a catalyst consisting of a support material, onto which at least one of the elements ruthenium, palladium, platinum, rhodium or iridium are applied in the form of a compound to give dimethyl ethers, methylalkyl ethers or methylaryl ethers. When a polyalkylene glycol is used as the starting reactant, its terminal hydroxymethyl groups are cleaved to produce the dimethyl ether of a glycol. Monoethylene glycol monomethyl ether, monoethylene glycol and ethanol are not produced from the hydrogenolysis of a polyalkylene glycol according to the teachings of this patent.

French Pat. No. 2,447,363 describes selectively cleaving polyalkylene glycol monoalkyl ethers at a carbon-to-oxygen covalent bond with molecular hydrogen in the presence of a nickel and barium catalyst to give alkylene glycol monoalkyl ethers and polyalkylene glycol monoalkyl ethers having one less ethylene group, e.g., diethylene glycol monoethyl ether is cleaved to give monoethylene glycol monoethyl ether. When hydrogenolysis of polyalkylene glycol monoalkyl ethers is not complete, small quantities of ethanol may be detected in the reaction mixture. This patent does not describe the hydrogenolysis of a polyalkylene glycol to produce each of monoethylene glycol monomethyl ether, monoethylene glycol and ethanol.

U.S. Pat. No. 3,833,634 describes a process for the preparation of polyfunctional oxygen-containing compounds such as ethylene glycol and/or derivatives thereof by reacting an oxide of carbon with hydrogen using a rhodium complex catalyst in combination with carbon monoxide at elevated temperature and pressure. Example 23 describes the production of ethylene glycol by hydrogenolysis of open chain glycol ethers, e.g., tetraethylene glycol dimethyl ether.

Japanese Public Disclosure No. 109,908/79 describes selectively cleaving an alkylene oxide, e.g., ethylene oxide, with molecular hydrogen in the presence of a hydrogenation catalyst and solvent having low polarity. The reaction is carried out in the liquid phase to give alkylene glycol alkyl ethers, e.g., monoethylene glycol monoethyl ether. Ethanol is produced as a by-product. This patent does not describe the hydrogenolysis of a polyalkylene glycol to produce each of monoethylene glycol monomethyl ether, monoethylene glycol and ethanol.

U.S. Pat. No. 1,953,548 describes a process for producing n-propyl alcohol by passing propylene oxide vapor over a contact catalyst containing alumina at elevated temperature and immediately thereafter, in the presence of hydrogen, over a hydrogenation catalyst containing reduced nickel.

U.S. Pat. No. 3,975,449 describes a hydrogenolysis process for producing a primary diol and/or triol from an epoxide by contacting the epoxide with molecular hydrogen and a solid catalyst comprising nickel or cobalt at elevated temperature and pressure.

Davidova and Kraus, *Journal of Catalysis*, 61, 1-6 (1980) describe cleaving of 1,2-epoxybutane with molecular hydrogen in the presence of a supported platinum catalyst at elevated temperature and atmospheric pressure to give oxygenated products, e.g., 2-butanone, 1-butanol and 2-butanol.

German Pat. No. 2,434,057 describes a hydrogenolysis method for producing glycol dimethyl ethers by cleaving the formals of the corresponding glycol monomethyl ethers with molecular hydrogen in the presence of catalysts composed of oxide mixtures of silicon and aluminum and/or rare earths and additionally containing the metals nickel, cobalt or copper.

German Pat. No. 2,716,690 describes a hydrogenolysis method for producing glycol dimethyl ethers by cleaving the formals of the corresponding glycol monomethyl ethers with molecular hydrogen in the presence of catalysts composed of oxide mixtures of silicon and aluminum and/or rare earths as well as metallic nickel and/or cobalt and/or copper, characterized by the fact that the catalysts additionally contain metallic palladium and/or rhodium and/or platinum as the promoter.

However, none of these references and no prior art is currently known to us which discloses or teaches a process for selectively cleaving a polyalkylene glycol at a carbon-to-oxygen covalent bond and independently at a carbon-to-carbon covalent bond by heating with molecular hydrogen in the presence of a hydrogenation catalyst containing ruthenium to produce at least one of monoethylene glycol monomethyl ether, monoethylene glycol and ethanol. Moreover, the production rate of each of said monoethylene glycol monomethyl ether, monoethylene glycol and ethanol is at least about 10 moles/kilogram ruthenium/hour.

DISCLOSURE OF INVENTION

The present invention provides a process for selectively cleaving a polyalkylene glycol, e.g., diethylene glycol, containing at least one ether group therein at a carbon-to-oxygen covalent bond and independently at a carbon-to-carbon covalent bond by heating the polyalkylene glycol with molecular hydrogen in the presence of a hydrogenation catalyst comprising ruthenium to produce at least one of monoethylene glycol monomethyl ether, monoethylene glycol and ethanol. The production rate of each of said monoethylene glycol monomethyl ether, monoethylene glycol and ethanol is at least about 10 moles/kilogram ruthenium/hour.

In copending U.S. patent application Ser. No. 307,226 filed on an even date herewith, there is described the manufacture of monoethylene glycol monomethyl ether, monoethylene glycol and ethanol by the hydrogenolysis of a polyalkylene glycol, e.g., diethylene glycol. The polyalkylene glycol is selectively cleaved at a carbon-to-oxygen covalent bond and independently at a carbon-to-carbon covalent bond by heating with molecular hydrogen in the presence of a hydrogenation catalyst comprising nickel to produce at least one of monoethylene glycol monomethyl ether, monoethylene glycol and ethanol. Monoethylene glycol monomethyl ether can be produced in predominant amounts by employing the process disclosed in this copending application.

Copending U.S. patent application Ser. No. 307,224, filed on an even date herewith, describes a process for selectively cleaving a polyalkylene glycol, e.g. diethylene glycol, at a carbon-to-oxygen covalent bond and independently at a carbon-to-carbon covalent bond by heating with molecular hydrogen in the presence of a hydrogenation catalyst comprising iridium to produce at least one of monoethylene glycol monoethyl ether, monoethylene glycol monomethyl ether, monoethylene glycol and ethanol. Monoethylene glycol monoethyl ether can be produced in significant amounts by employing the process disclosed in this copending application.

In copending U.S. patent application Ser. No. 307,210 filed on an even date herewith, there is described the manufacture of monoethylene glycol and ethanol by the hydrogenolysis of a polyalkylene glycol, e.g., diethylene glycol. The polyalkylene glycol is cleaved at a carbon-to-oxygen covalent bond by heating with molecular hydrogen in the presence of a hydrogenation catalyst, e.g., copper chromite, to produce at least one of monoethylene glycol and ethanol.

It has been suprisingly found as a result of the present invention that when a composition containing ruthenium is used as the hydrogenation catalyst in a process for hydrogenolyzing polyalkylene glycols, each of monoethylene glycol monomethyl ether, monoethylene glycol and ethanol is formed at a production rate of at least about 10 moles/kilogram ruthenium/hour. This exceptional production rate is sufficiently high to be of commercial interest. By employing the hydrogenolysis process of the instant invention, significant amounts of monoethylene glycol monomethyl ether, monoethylene glycol and ethanol may be produced in a given time period relative to the small amount of active metal, i.e., ruthenium, employed in the hydrogenation catalyst. The economic advantages in terms of the cost of the relatively small amounts of active metal, i.e., ruthenium, required for the hydrogenation catalyst to achieve the given reaction at exceptional production rates are readily apparent.

DETAILED DESCRIPTION

Hydrogenolysis of polyalkylene glycols may proceed according to different cleavage pathways. For example, as illustrated in the present invention, polyalkylene glycols may be cleaved at either a carbon-to-oxygen covalent bond or a carbon-to-carbon covalent bond to give different products. The cleavage pathways are influenced or varied, to a certain extent, by choice of hydrogenation catalyst, concentration of active metal in hydrogenation catalyst, pressure provided by molecular hydrogen and other factors. When a hydrogenation catalyst containing ruthenium is used in the hydrogenolysis of a polyalkylene glycol, e.g., diethylene glycol, according to the present invention, the cleavage pathway may be about equally directed toward a carbon-to-oxygen covalent bond and independently toward a carbon-to-carbon covalent bond resulting in the production of monoethylene glycol monomethyl ether, and monoethylene glycol in near equimolar amounts and ethanol in lesser amounts. However, by varying the concentration of active metal, i.e., ruthenium, in the hydrogenation catalyst and/or varying certain reaction conditions, e.g., pressure resulting from molecular hydrogen, temperature, etc., the cleavage pathway may be predominantly directed toward either a carbon-to-oxygen covalent bond or a carbon-to-carbon covalent bond to give monoethylene glycol-ethanol in predominant amounts or monoethylene glycol monomethyl ether in predominant amounts respectively. As a preferred embodiment of the present invention, at least one of monoethylene glycol monomethyl ether, monoethylene glycol and ethanol is produced from the hydrogenolysis or cleaving of a polyalkykene glycol, e.g., diethylene glycol. The production rate of each of monoethylene glycol monomethyl ether, monoethylene glycol and ethanol is at least about 10 moles/kilogram ruthenium/hour.

The preferred hydrogenation catalysts which can be used to catalyze the hydrogenolysis process of this invention are well known in the art and include compositions containing ruthenium. The preferred hydrogenation catalysts may also include, as an additional ingredient, a promoter or promoters for increasing the activity of the hydrogenation catalysts. Suitable catalyst promoters may include barium, calcium, magnesium, manganese, strontium, zirconium, titanium, hafnium, potassium, lithium, sodium, rubidium, cesium, molybdenum, chromium, tungsten, zinc and the like. Certain metals such as copper, chromium, molybdenum, tungsten, iron, cobalt, nickel, rhodium, palladium, platinum, iridium, rhenium, tantalum, vanadium, niobium, zinc and the like may act as co-catalysts in combination with ruthenium. It is noted that molybdenum, chromium, tungsten and zinc may act as either a co-catalyst or promoter. Reference to the hydrogenation catalysts, promoters and co-catalysts as containing the above-described metals is meant to include the metal in the compound form as well as the elemental form, for example as a metal oxide or sulfide or as a metal hydride, or as the reduced elemental metal or as mixtures of the foregoing. The hydrogenation catalysts may be employed in the presence or absence of a catalyst support. Suitable catalyst supports include silica gel, aluminum oxide, magnesium oxide, titanium dioxide, magnesium aluminate, zirconium dioxide, silicon carbide, ceramic, pumice, carbon, diatomaceous earth, kieselguhr and the like. Illustrative of the preferred hydrogenation catalysts useful in the process of this invention include compositions containing ruthenium on a suitable catalyst support, e.g., ruthenium on carbon, ruthenium on magnesium oxide, ruthenium on silica gel, ruthenium on titanium dioxide, ruthenium on aluminum oxide and the like. The compositions containing oxides may be totally or partially reduced in situ during reactor heat-up. The most preferred hydrogenation catalysts of this invention include compositions containing about 5 percent by weight ruthenium on a suitable catalyst support. Many of the above-described hydrogenation catalysts are commercially available and others are prepared by known methods detailed hereinbelow.

The hydrogenation catalysts useful in the process of this invention can be employed in any form. They may be present in the reaction mixture as finely divided powders, porous tablets, pellets, spheres, granules and the like. It is desirable that the hydrogenation catalysts possess a high surface area to provide preferred reaction rates. The preferred surface area ranges from about 0.5 m$^2$/gm to about 400 m$^2$/gm and even greater. Most preferably, the surface area of the hydrogenation catalysts ranges from about 10 m$^2$/gm to about 400 m$^2$/gm. The average pore diameter of the hydrogenation catalysts is not narrowly critical. Hydrogen diffusion appears to be rate limiting in catalysts having very small pores. It also appears that a very small average pore diameter and/or a large catalyst particle diameter are detrimental to high monoethylene glycol monomethyl ether-monoethylene glycol-ethanol selectivities and/or polyalkylene glycol conversion rates. In general, for obtaining desirable monoethylene glycol monomethyl ether-monoethylene glycol-ethanol selectivities, it is believed that catalysts having an average pore diameter of at least about 150 °Å, preferably at least about 250 °Å, and a particle diameter of less than 10 millimeters, preferably 5 millimeters or less, are useful in the hydrogenolysis process of this invention.

The quantity of the hydrogenation catalyst which is employed is not narrowly critical and can vary over a wide range. In general, the process of this invention is desirably conducted either continuously or batchwise in the presence of a catalytically effective quantity of the hydrogenation catalyst which gives a production rate for each of monoethylene glycol monomethyl ether, monoethylene glycol and ethanol of at least about 10 moles/kilogram ruthenium/hour. The reaction proceeds when one employs as little as about 0.01 weight percent, or even a lesser amount of catalyst based on the total quantity of the reaction mixture under batch conditions. The upper concentration of the hydrogenation catalyst can be quite high, e.g., about 50 weight percent of catalyst based on the total quantity of reaction mixture. Higher concentrations may be used if desired. However, the upper concentration appears to be dictated by economics in terms of the cost of certain hydrogenation catalysts to achieve the given reaction and by ease of handling of the reaction mixture during the course of the reaction. Depending on various factors, such as the total operative pressure of the system, the operative temperature and other considerations, a concentration of between about 0.1 and about 30 weight percent hydrogenation catalyst based on the total quantity of the reaction mixture is generally suitable in the practice of this invention.

The preferred polyalkylene glycols which can be used in the practice of the process of this invention are well known in the art and include: diethylene glycol, triethylene glycol, tetraethylene glycol and the like. In the most preferred embodiment of this invention, diethylene glycol formed as a by-product of the commercial oxide/glycol process described hereinabove, is selectively cleaved at a carbon-to-oxygen covalent bond and independently at a carbon-to-carbon covalent bond by heating with molecular hydrogen in the presence of a hydrogenation catalyst containing ruthenium to produce at least one of monoethylene glycol monomethyl ether, monoethylene glycol and ethanol. The production rate of each of said monoethylene glycol monomethyl ether, monoethylene glycol and ethanol is at least about 10 moles/kilogram ruthenium/hour. By utilizing the preferred catalysts and reaction conditions of the present invention, higher polyalkylene glycols such as triethylene glycol and tetraethylene glycol may be selectively cleaved to give at least one of monoethylene glycol monomethyl ether, monoethylene glycol and ethanol at a production rate for each of at least 10 moles/kilogram ruthenium/hour. These polyalkylene glycols are prepared by methods well known in the art.

The relative amounts of polyalkylene glycol and molecular hydrogen which are initially present in the reaction mixture can be varied over a wide range. In general, the molar ratio of molecular hydrogen to polyalkylene glycol is in the range of between about 1:20 to about 2000:1, preferably between about 1:2 and about 500:1 and most preferably, between 1:1 and about 200:1. It is to be understood, however, that molar ratios outside the stated broad range may be employed. However, very high molecular hydrogen-to-polyalkylene glycol molar ratios are economically unattractive, and very low molecular hydrogen-to-polyalkylene glycol molar ratios will result generally in low conversions and lower product selectivities. When operating in the continuous mode, molecular hydrogen and polyalkylene glycol may be fed either concurrently or countercurrently over the hydrogenation catalyst using either upward, downward or horizontal flow with concurrent downward flow being preferred. The gas hourly space velocity (GHSV) of molecular hydrogen and the liquid hourly space velocity (LHSV) of polyalkylene glycol may be varied over a wide range utilizing the continuous process. The gas hourly space velocity of molecular hydrogen may range from about 100 hr$^{-1}$ or less to greater than 100,000 hr$^{-1}$, preferably from about 1,000 hr$^{-1}$ to about 100,000 hr$^{-1}$, and most preferably from about 2,000 hr$^{-1}$ to about 75,000 hr$^{-1}$. The liquid hourly space velocity of polyalkylene glycol may range from about 0.01 hr$^{-1}$ or less to about 100 hr$^{-1}$ or greater, preferably from about 0.1 hr$^{-1}$ to about 25 hr$^{-1}$, and most preferably from about 0.25 hr$^{-1}$ to about 10 hr$^{-1}$. The higher GHSV and LHSV values generally tend to result in uneconomically low conversion of polyalkylene glycol, and the lower GHSV and LHSV values generally tend to decrease the selectivity of monoethylene glycol monomethyl ether, monoethylene glycol and ethanol. The intended purpose is to provide a sufficient quantity of polyalkylene glycol and molecular hydrogen in the reaction mixture to effect the desired production of monoethylene glycol monomethyl ether, monoethylene glycol and ethanol at a production rate for each of at least about 10 moles/kilogram ruthenium/hour.

The process of this invention can be effected over a wide temperature range. In general, the process is conducted at a temperature of between about 125° C. and about 350° C. Lower temperatures generally give improved product selectivity, but often at undesirable low production rates. Higher temperatures generally increase total productivity but tend to increase by-product formation. Operating the process at temperatures lower than 125° C. will result in undesirably low production rates so that the reaction will typically be operated over an extended period of time and/or excessive quantities of catalyst must be employed in order to obtain the desired production of reaction products. When operating the process at temperatures higher than 350° C. there is a tendency for the organic materials contained in the reaction mixture to decompose. In most cases when operating at the lower end of the temperature range, it is desirable to utilize pressures in the higher end of the pressure range. The preferred temperature range is between about 150° C. and 300° C., while the most preferred temperature range is between about 175° C. and 265° C. However, there are occasions when a preferred temperature range may include any of the more desirable ranges as well as the broadest range such that the process may be operated at a temperature of between 150° C. and 300° C. as well as between about 125° C. and 325° C.

The process of the present invention is effected under atmospheric or superatmospheric pressure conditions. In a preferred embodiment of the present invention, the pressure is produced almost exclusively by the molecular hydrogen provided to the reaction. However, suitable inert gaseous diluents may also be employed if desired. Actual operating pressures (initial pressures under batch operating conditions) of between about atmospheric and about 10,000 psig represent an operative limit for producing the monoethylene glycol monomethyl ether, monoethylene glycol and ethanol products. The preferred actual operating pressure conditions for the production of monoethylene glycol monomethyl ether range from about 100 psig to about 4000 psig and, most preferably, from about 250 psig to about 2000 psig. When operating the process at lower pressures, the rate of production of the desired products becomes slower and therefore the reaction period must be extended until the desired amount of reaction products are produced. When operating the process at higher pressures, the rate of production of the desired products will be increased. Higher pressures generally tend to increase the selectivity to monoethylene glycol monomethyl ether, but very high pressures can also increase by-product formation through secondary hydrogenolysis reactions. Lower pressures generally tend to increase the selectivity of monoethylene glycol and ethanol, increase the formation of by-products such as 2-oxodioxane and decrease the selectivity of monoethylene glycol monomethyl ether.

The process of this invention is effected for a period of time sufficient to produce the desired monoethylene glycol monomethyl ether, monoethylene glycol and ethanol at a production rate for each of at least about 10 moles/kilogram ruthenium/hour. In general, the reaction time can vary from a fraction of a second to several hours, i.e., from 0.1 second and shorter to approximately 10 hours, and longer. When operating the hydrogenolysis process of this invention under continuous conditions, the reaction time or residence period may generally range from a fraction of a second to several minutes or more whereas the residence period under batch conditions may enerally range from a few minutes to several hours. It is readily appreciated that the required residence period will be influenced by reaction temperature, concentration and choice of hydrogenation catalyst, total pressure, concentration (molar ratio) of polyalkylene glycol and molecular hydrogen and other factors. The synthesis of the desired products, i.e., monoethylene glycol monomethyl ether, monoethylene glycol and ethanol, from the hydrogenolysis of a polyalkylene glycol is suitably conducted under operative conditions which give a production rate for each of at least 10 moles/kilogram ruthenium/hour.

The process of this invention can be carried out in a batch, semi-continuous or continuous manner in either a liquid phase, vapor phase or a combination liquid-vapor phase. The reaction may be conducted in fixed-bed, slurry-phase, trickle-bed or fluidized bed reactors or the like using a single reaction zone or a plurality of reaction zones, in series or in parallel. The reaction may be conducted intermittently or continuously in an elongated tubular zone or a series of such zones. The material of construction of the equipment should be such so as to be inert during the reaction. The equipment should also be able to withstand the reaction temperatures and pressures. The reaction zone can be fitted with internal and/or external heat exchangers to control undue temperature fluctuations caused by the moderate exothermic nature of the reaction. In a preferred embodiment of the present invention, agitation means to ensure complete mixing of the reaction mixture should be used in reaction systems not employing a fixed-bed catalyst. Mixing induced by magnetic stirrer, vibration, shaker, rotating, sparging with gas, oscillation, etc. are all illustrative of the types of agitation means which are contemplated herein. Such agitation means are available and well known to the art.

The polyalkylene glycol, molecular hydrogen and hydrogenation catalyst ingredients may be initially introduced into the reaction zone batchwise. Alternatively, the polyalkylene glycol, molecular hydrogen and hydrogenation catalyst ingredients may be introduced into the reaction zone continuously or intermittently during the course of the synthesis reaction. Means to introduce the ingredients into the reaction zone during the course of the reaction and/or means to adjust the ingredients in the reaction zone during the reaction, either intermittently or continuously, can be conveniently utilized in the process to maintain the desired molar ratios of ingredients and to maintain the pressure exerted by hydrogen.

The operative conditions of the present process may be adjusted to optimize the conversion rate of polyalkylene glycol, the selectivities and production rates of the desired products and/or the economics of the process. For example, it may generally be preferred to operate at relatively low conversion rates, which tends to increase selectivities of monoethylene glycol monomethyl ether, monoethylene glycol and ethanol and increase the monoethylene glycol/ethanol molar ratio by reducing secondary hydrogenolysis reactions. Recovery of the desired monoethylene glycol monomethyl ether, monoethylene glycol and ethanol can be achieved by methods well known in the art, such as by distillation, fractionation, extraction, and the like. Typically, in carrying out the process, the product contained in the reaction mixture would be withdrawn from the reaction zone and distilled to recover the desired products. For reactors not employing a fixed-bed catalyst, a fraction comprising the hydrogenation catalyst and by-products can be removed for recovery or regeneration of the catalyst. Fresh hydrogenation catalyst can be intermittently added to the reaction stream or it can be added directly to the reaction zone, to replenish any catalyst which is lost in the process.

Although this invention has been described with respect to a number of details, it is not intended that this invention should be limited thereby. The examples which follow are intended solely to illustrate the embodiments of this invention which to date have been determined and are not intended in any way to limit the scope of this invention.

As used in the Examples appearing hereinafter, the following designations, terms and abbreviations have the indicated meanings:

psig: pounds per square inch gauge pressure.
rpm: revolutions per minute.
kg: kilogram
cat.: catalyst
hr.: hour
lbs.: pounds
cu.: cubic
ft.: foot
cc: cubic centimeter
gm: gram
m$^2$: square meter
DEG: diethylene glycol
conv.: conversion
% or percent: percent by weight unless otherwise specified.
ratios: a weight basis unless otherwise specified.
temperatures: are given in ° C. unless otherwise specified.
ND: not detected
selectivity: calculated according to the formula, $$\% \text{ Selectivity } i = \frac{r_i \times 100}{r_{DEG \text{ conv.}}}$$

where i is the individual component, i.e., monoethylene glycol monomethyl ether, monoethylene glycol, ethanol or by-products and r is the rate in moles/kg Ru/hr.

The catalysts used in the Examples are identified as follows:

Catalyst I. A composition containing 5 percent by weight ruthenium on carbon and sold by J. Bishop.

Catalyst II. A composition containing 0.5 percent by weight ruthenium on carbon and sold by Engelhard.

Catalyst III. A composition containing 2.5 percent by weight ruthenium on magnesium oxide; and having a surface area of 125 m$^2$/gm, a bulk density of 44 lbs./cu. ft., a particle size of ⅛ inch by 3/16 inch and a pore volume of 0.44 cc/gm.

Catalyst IV. A composition containing 5 percent by weight ruthenium and 0.2 percent by weight calcium on silica gel; the silica gel is commercially available from Davison Specialty Chemical Company as Grade-59; and having a surface area of 275 m$^2$/gm, a bulk density of 25 lbs./cu. ft., the particle size is powder after grinding and a pore volume of 1.2 cc/gm.

Catalyst V. A composition containing 5 percent by weight ruthenium on silica gel; the silica gel is commercially available from Davison Specialty Chemical Company as Grade-59; and having a surface area of 275 m$^2$/gm, a bulk density of 25 lbs./cu. ft., the particle size is powder after grinding and a pore volume of 1.2 cc/gm.

Catalyst VI. A composition containing 5 percent by weight ruthenium on titanium dioxide; the titanium dioxide is commercially available from Harshaw as Ti-0702T; and having a surface area of 135 m$^2$/gm, a bulk density of 72 lbs./cu. ft., a particle size of ⅛ inch and a pore volume of 0.24 cc/gm.

Catalyst VII. A composition containing 1 percent by weight ruthenium on aluminum oxide; the aluminum oxide (gamma alumina) is commercially available from Kaiser Aluminum Company as KA-201; and having a particle size of ⅛ inch by 3/16 inch.

Commercially available catalysts, i.e., Catalysts I and II, were used in the Examples as supplied from the manufacturer. The pelleted versions were first pulverized using a mortar and pestle until each catalyst could pass through a 200-mesh screen. Catalyst reduction, where necessary, was accomplished in situ during reactor heat-up.

Catalyst III was prepared in the laboratory in accordance with the following procedure:

The support was impregnated under vacuum with a warm (70° C.–80° C.) toluene solution of ruthenium acetonyl acetonate complex. The solution volume was just sufficient to fill the catalyst pores, and the weight of dissolved ruthenium complex was adjusted to give the indicated weight percent ruthenium in the finished catalyst. After standing 30 minutes at room temperature the solvent was evaporated in a nitrogen-purged oven by heating in stages, i.e., 85° C. for 1 hour, 115° C. for 2 hours, 150° C. for 2 hours and 200° C. for 2 hours. The dried impregnated support was transferred to a quartz tube and heated rapidly to 500° C. in a stream of 50:50 ratio air and nitrogen. Heating at 500° C. was continued for 3 hours under 100% air to complete oxidation of the complex, then the system was flushed thoroughly with nitrogen. The nitrogen was replaced by a stream of 100% hydrogen introduced at 500° C. and maintained for three hours. The catalyst was cooled to 80° C. under hydrogen, then cooled to room temperature under a nitrogen purge.

Catalysts IV, V and VI were prepared in the laboratory in accordance with the following procedure:

The support, which was prewashed with hot oxalic acid solution to reduce impurities in the case of Catalysts IV and V (silica gel), was impregnated under vacuum with an aqueous solution of appropriate precursors denoted in Table A below. The solution volume was just sufficient to fill the catalyst pores, and the salt concentration was adjusted to give the desired weight percent in the finished catalyst. After standing 30 minutes at room temperature, the impregnated support of Catalyst IV was dried in stages as follows: 85° C. for 1 hour, 110° C. for 2 hours, and 150° C. for 3 hours; the impregnated support of Catalyst V was dried in the following stages: 85° C. for 1 hour, 110° C. for 2 hours, 150° C. for 2 hours and 200° C. for 2 hours; and the impregnated support of Catalyst VI was dried in the following stages: 85° C. for 1 hour, 110° C. for 2 hours and 150° C. for 2 hours. The dried material was transferred to a quartz tube, and reduced by heating to 500° C. at a rate of 100° C. per hour under flowing hydrogen. The temperature was held at 500° C. for 1 hour and then the system was cooled to 80° C. in hydrogen. The hydrogen was displaced with nitrogen and the catalyst cooled to room temperature.

TABLE A

| Catalyst Identification | Catalyst Precursors |
|---|---|
| Catalyst IV | RuCl$_3$, Ca(NO$_3$)$_2$ |
| Catalyst V | RuCl$_3$ |
| Catalyst VI | RuCl$_3$ |

Catalyst VII was prepared in the laboratory in accordance with the following procedure:

The aluminum oxide support was broken and sieved to 6–10 mesh. The support was then heated to 600° C. in flowing nitrogen for 6 hours followed by heating at 500° C. in air overnight. After cooling, the dried support was covered with a solution of Ru (CO)$_{12}$ in a minimum of n-pentane. The n-pentane was evaporated over a 3-hour period by warming in a hot water bath with a stream of nitrogen slowly flowing through the system. The remaining solid material was then warmed for 1 hour under vacuum to remove the last traces of n-pentane. The dried solid material was reduced with 100 percent hydrogen by heating to 300° C. at a rate of 100° C. per hour. After holding the temperature at 300° C. for 2 hours, the system was then cooled to 80° C. in hydrogen. The hydrogen was displaced with nitrogen and the catalyst cooled to room temperature.

EXAMPLES 1 THROUGH 15

Examples 1 through 15 were conducted batchwise in a 300-milliliter stainless-steel autoclave reactor equipped with a magnetic stirrer in accordance with the following procedure. Prior to each of the examples the magnetic stirrer was disassembled and all components washed thoroughly to remove residual catalyst powder. All parts and internals of the reactor were similarly cleaned, rinsed with acetone and dried. The reactor was charged with a mixture of 50 grams of diethylene glycol and 1 gram of a finely pulverized catalyst specifically identified for each example in Table I below. (The reactor was charged with only 25 grams of diethylene glycol in Examples 4 and 5 and with 100 grams of diethylene glycol in Example 10. The catalyst charge in Example 5 was only 0.5 grams.) The reactor was then sealed, purged twice with 500 psig of molecular hydrogen and, after pressure testing, charged with an initial amount of molecular hydrogen. The initial molecular hydrogen pressure for each example is given in Table I. The magnetic stirrer was started and adjusted to 1000 rpm, and the reaction system was then heated to a temperature specified for each example in Table I. After a six-hour reaction period the reactor was cooled, stirring was discontinued and the pressure vented slowly. (The reaction period was only two hours for Example 5.) During the venting step, a sample of product gas was collected for analysis by gas chromatography. The remaining liquid contents of the reactor were then removed, weighed and analyzed by gas chromatography. The performance of catalysts tested in Examples 1 through 15 is given in Table I.

TABLE I

POLYALKYLENE GLYCOL HYDROGENOLYSIS
(BATCH PROCESS)
PRODUCT DATA

| EXAMPLE | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Catalyst Identification | I | I | I | I | I | I | I | I | I | II | III | IV | V | VI | VII |
| Temperature, °C. | 200 | 200 | 250 | 250 | 250 | 250 | 175 | 200 | 225 | 250 | 250 | 250 | 250 | 250 | 250 |
| Initial Pressure (H$_2$), psig | 250 | 250 | 500 | 1,000 | 1,000 | 2,000 | 2,000 | 2,000 | 2,000 | 1,000 | 2,000 | 2,000 | 2000 | 2000 | 2000 |
| Reaction Rate (moles/kg/hr) to: | | | | | | | | | | | | | | | |
| Monoethylene Glycol | 104 | 166 | 172 | 94 | 668 | 240 | 162 | 242 | 168 | 48 | 276 | 192 | 158 | 200 | 460 |
| Ethanol | 12.8 | 20 | 22 | 12.4 | 40 | 25.4 | 22 | 56 | 42 | 16 | 156 | 46 | 46 | 68 | 180 |
| Ethane | ND | ND | 32.4 | 70.6 | 119.6 | 89 | 53.2 | 300 | 1234 | .4 | 179.6 | 354 | 296.8 | 272 | 84 |
| Monoethylene Glycol Monomethyl Ether | 46 | 96 | 106 | 302 | 942 | 274 | 148 | 270 | 166 | 40 | 136 | 162 | 132 | 180 | 640 |
| Monoethylene Glycol Monoethyl Ether | .4 | 1 | 2.2 | 10.8 | 50 | 8.2 | 46 | 108 | 110 | 10 | 148 | 58 | 12.6 | 19.6 | 47 |
| Methanol | 5.4 | 24 | 25.8 | 62.4 | 103.8 | 89.6 | 15.2 | 50.4 | 45.6 | ND | 32.8 | 53 | 66.6 | 79.6 | 150 |
| Dioxane | 1.8 | ND | 11.8 | 2.8 | 3.2 | 3.4 | ND | ND | ND | 148 | ND | ND | 20 | 26 | 73 |
| 2-Oxodioxane | 1.8 | .6 | 4.4 | ND | 5.2 | 2 | ND | ND | 1.2 | ND | ND | 1.6 | 9.8 | 2.8 | ND |
| 1,2-Butanediol[a] | ND | ND | 2.2 | 8 | ND | 1.4 | ND | ND | 1.0 | ND | 1.2 | 1.4 | 16 | 13 | 60 |
| Others[b] | 25.2 | 17.6 | 21.8 | 6.2 | 8.4 | 11.8 | 3 | 14.4 | 28 | ND | 12 | 10 | 52 | 60 | 5 |
| Selectivity (mole percent) | | | | | | | | | | | | | | | |
| Monoethylene Glycol Monomethyl Ether | 34 | 46 | 41 | 72 | 66 | 57 | 47 | 39 | 16 | 17 | 22 | 31 | 27 | 32 | 54 |

TABLE I-continued

POLYALKYLENE GLYCOL HYDROGENOLYSIS
(BATCH PROCESS)
PRODUCT DATA

| EXAMPLE | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Monoethylene Glycol | 78 | 80 | 66 | 22 | 47 | 50 | 51 | 35 | 16 | 21 | 46 | 36 | 32 | 34 | 38 |
| Ethanol | 10 | 10 | 8 | 3 | 3 | 5 | 7 | 8 | 4 | 7 | 26 | 9 | 9 | 12 | 15 |

(a)Small amounts of 4-butyrolactone and diethylene glycol monoethyl ether may also be included in this value.
(b)Includes n-butanol, acetaldehyde, diethyl ether, dimethyl ether, 2-methyldioxolane, 2,3,-butanediol, propylene glycol, triethylene glycol and unknowns.

Examples 1 through 15 illustrate the overall effectiveness of compositions containing ruthenium as the hydrogenation catalyst of the present invention. Compositions containing about 5 percent by weight ruthenium are the most preferred hydrogenation catalysts for use in the hydrogenolysis process of this invention. When a composition containing ruthenium is used as the hydrogenation catalyst, monoethylene glycol monomethyl ether, monoethylene glycol and ethanol are formed at a production rate for each of at least about 10 moles/kilogram ruthenium/hour. Examples 5 and 15 show exceptional production rates for monoethylene glycol monomethyl ether, monoethylene glycol and ethanol. In Example 5, monoethylene glycol monomethyl ether is formed at a production rate of 942 moles/kilogram ruthenium/hour, monoethylene glycol is formed at a production rate of 668 moles/kilogram ruthenium/hour and ethanol is formed at a production rate of 40 moles/kilogram ruthenium/hour. In Example 15, monoethylene glycol monomethyl ether is formed at a production rate of 640 moles/kilogram ruthenium/hour, monoethylene glycol is formed at a production rate of 460 moles/kilogram ruthenium/hour and ethanol is formed at a production rate of 180 moles/kilogram ruthenium/hour. These exceptional production rates are sufficiently high to be of highly desirable commercial interest. Significant amounts of monoethylene glycol monomethyl ether, monoethylene glycol and ethanol are produced in a given time period relative to the small amount of active metal, i.e., ruthenium, employed in the hydrogenation catalyst by using the hydrogenolysis process of the instant invention. The economic advantages in terms of the cost of the relatively small amounts of active metal, i.e., ruthenium, required for the hydrogenation catalyst to achieve the given reaction at exceptional production rates are readily apparent.

Examples 3, 4, 5 and 6 illustrate the effect of pressure on the hydrogenolysis reaction using the same hydrogenation catalyst, i.e., Catalyst I, and the same temperature. As can be seen from Example 5, a pressure of about 1000 psig is desirable for obtaining overall preferable performance. The most preferred pressure for monoethylene glycol monomethyl ether, monoethylene glycol and ethanol formation at a production rate for each of at least about 10 moles/kilogram ruthenium/hour ranges from about 250 psig to about 2000 psig.

Examples 6, 7, 8 and 9 illustrate the effect of temperature on the hydrogenolysis reaction using the same hydrogenation catalyst, i.e., Catalyst I, and the same pressure. As can be seen from these examples, a temperature ranging from about 175° C. to about 250° C. is highly desirable for obtaining overall preferred performance. The most preferred temperature for the formation for each of monoethylene glycol monomethyl ether, monoethylene glycol and ethanol at a production rate of at least about 10 moles/kilogram ruthenium/hour ranges from about 175° C. to about 265° C.

Examples 10 through 15 illustrate the effect of other compositions containing ruthenium as the preferred hydrogenation catalyst utilized in the hydrogenolysis process of this invention.

I claim:

1. A process for making monoethylene glycol monomethyl ether, monoethylene glycol and ethanol from polyethylene glycol comprising providing said polyethylene glycol with molecular hydrogen under hydrogenolysis conditions including elevated temperature and the presence of hydrogenation catalyst comprising ruthenium, sufficient to cleave said polyethylene glycol both at a carbon-to-oxygen covalen bond to produce ethanol and at a carbon-to-carbon covalent bond.

2. The process of claim 1 wherein the hydrogenolysis conditions are maintained for a time sufficient that each of monoethylene glycol monomethyl ether, monoethylene glycol and ethanol are produced at a rate of at least about 10 moles/kilogram rutheinum/hour.

3. The process of claim 1 wherein the polyethylene glycol is diethylene glycol.

4. The process of claim 1 wherein the hydrogenation catalyst is a composition comprising about 5 percent by weight ruthenium.

5. The process of claim 1 wherein the polyethylene glycol and molecular hydrogen are present in a molar ratio of molecular hydrogen to polyethylene glycol of from about 1:20 to about 2000:1.

6. The process of claim 1 wherein the hydrogenation catalyst is present in an amount of from about 0.01 weight percent to about 50 weight percent based on the total weight of the reaction mixture.

7. The process of claim 1 wherein the reaction temperature is from about 125° C. to about 350° C.

8. The process of claim 1 wherein the initial pressure resulting from molecular hydrogen is from about 100 psig to about 4000 psig.

* * * * *